US010856992B2

(12) United States Patent
Ferro et al.

(10) Patent No.: US 10,856,992 B2
(45) Date of Patent: Dec. 8, 2020

(54) IMPLANT DEVICE(S) INCLUDING TAPERED PROTRUSIONS AND METHOD(S) FOR INSERTING THE SAME INTO BONE

(71) Applicant: AOD Holdings, LLC, Arroyo Grande, CA (US)

(72) Inventors: Thomas D. Ferro, Arroyo Grande, CA (US); Joseph R. Phillips, Arroyo Grande, CA (US); Austin T. Ferro, Arroyo Grande, CA (US)

(73) Assignee: AOD Holdings, LLC, Arroyo Grande, CA (US)

( * ) Notice: Subject to any disclaimer, the term of this patent is extended or adjusted under 35 U.S.C. 154(b) by 0 days.

(21) Appl. No.: 15/498,896

(22) Filed: Apr. 27, 2017

(65) Prior Publication Data

US 2017/0312084 A1    Nov. 2, 2017

Related U.S. Application Data

(60) Provisional application No. 62/328,440, filed on Apr. 27, 2016.

(51) Int. Cl.
  *A61F 2/02* (2006.01)
  *A61F 2/38* (2006.01)
  (Continued)

(52) U.S. Cl.
  CPC ........ *A61F 2/3859* (2013.01); *A61F 2/30771* (2013.01); *A61F 2/3662* (2013.01); *A61F 2/389* (2013.01); *A61F 2/461* (2013.01); *A61F 2002/3093* (2013.01); *A61F 2002/30841* (2013.01); *A61F 2002/30845* (2013.01);
  (Continued)

(58) Field of Classification Search
  CPC .......... A61F 2/4611; A61F 2310/00023; A61F 2002/30841; A61F 2/442; A61F 2002/30904; A61F 2220/0016; A61F 2002/30622; A61F 2002/30266; A61F 2220/0008
  See application file for complete search history.

(56) References Cited

U.S. PATENT DOCUMENTS

| 6,447,544 B1 * | 9/2002 | Michelson .......... A61F 2/30744 623/17.16 |
| 2008/0154378 A1 * | 6/2008 | Pelo ..................... A61B 17/866 623/17.16 |

(Continued)

OTHER PUBLICATIONS

Smith & Nephew, Surgical Techniques, Journey II UNI Unicompartmental Knee System, 2015.

*Primary Examiner* — Ann Schillinger
(74) *Attorney, Agent, or Firm* — McDonnell Boehnen Hulbert & Berghoff LLP

(57) ABSTRACT

An example implant device includes a base having a surface that mates with bone, and a plurality of tapered protrusions positioned on the base and extending from the surface of the base that mates with bone. A surface of the plurality of tapered protrusions includes a textured surface to increase area for bone growth. An example method for inserting the implant device into bone includes forcing the plurality of tapered protrusions of the implant device into the bone, and securing the implant device in place without cement due to the plurality of tapered protrusions cutting into the bone for fixation of the implant device.

22 Claims, 12 Drawing Sheets

(51) Int. Cl.
*A61F 2/36* (2006.01)
*A61F 2/46* (2006.01)
*A61F 2/30* (2006.01)

(52) U.S. Cl.
CPC ............... *A61F 2002/30878* (2013.01); *A61F 2002/3895* (2013.01); *A61F 2002/4628* (2013.01); *A61F 2002/4681* (2013.01)

(56) References Cited

U.S. PATENT DOCUMENTS

2011/0218641 A1* 9/2011 Smith ................. A61F 2/32
 623/22.42
2013/0110255 A1* 5/2013 Picha ................. A61L 27/04
 623/23.74

* cited by examiner

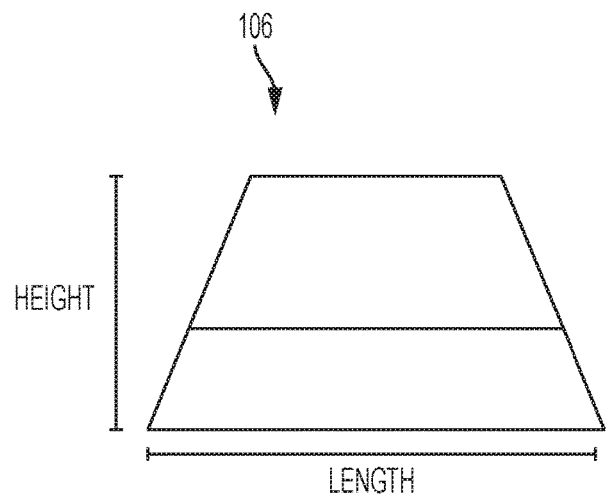
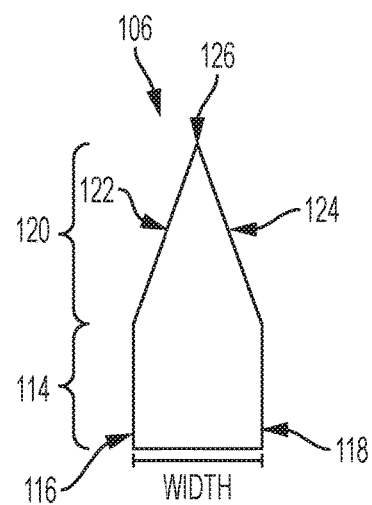
FIG. 5    FIG. 6
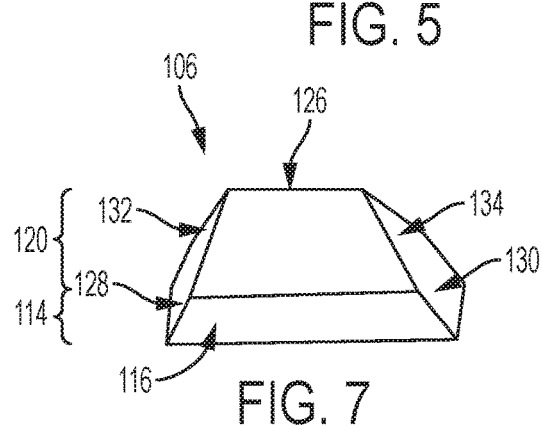
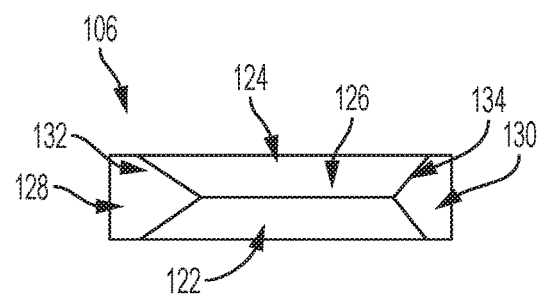
FIG. 7    FIG. 8
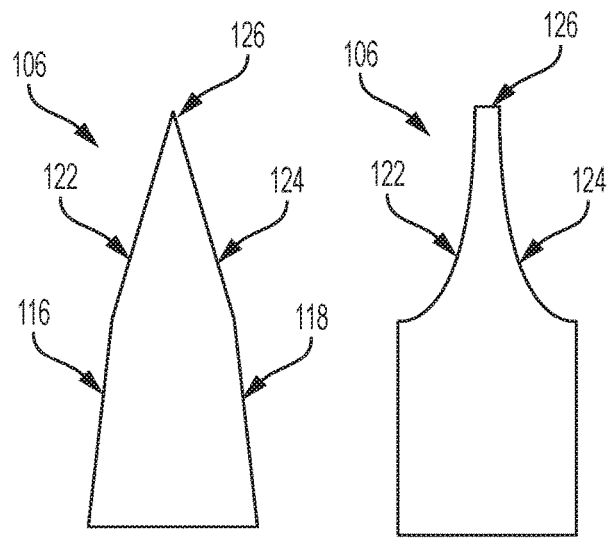
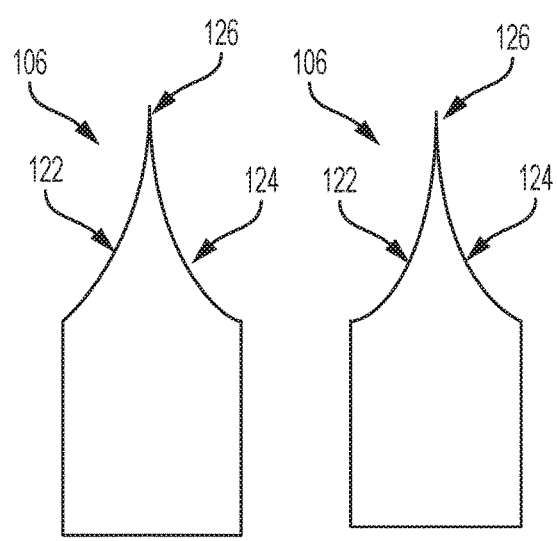
FIG. 9    FIG. 10    FIG. 11    FIG. 12

IMPLANT DEVICE(S) INCLUDING TAPERED PROTRUSIONS AND METHOD(S) FOR INSERTING THE SAME INTO BONE

CROSS REFERENCE TO RELATED APPLICATION

This patent application claims priority to U.S. provisional patent application 62/328,440, filed on Apr. 27, 2016, the entire contents of which are herein incorporated by reference.

FIELD

The present disclosure relates generally to implant devices and methods for fixing implant devices to a bone without using adhesives or cement, and more particularly to cementless implant devices, such as a cementless unicompartmental knee replacement (UKA) implant device, and a cementless total knee replacement implant device (TKA).

BACKGROUND

Unicompartmental knee arthroplasty (hereafter referred to as UKA), is a minimalistic knee replacement procedure that allows the alteration of only one of the condylar surfaces of the knee. The outcome of this surgical procedure is sometimes negatively affected by the migration, loosening or shifting of the femoral or tibial prosthesis (hereafter referred to as a UNI implant). Surgeons commonly use a polymer/monomer mixture to assist in affixing the prosthesis to the patient's bone surface to prevent these problems. But, use of such adhesives presents different problems themselves. Similar adhesives are used to affix many other types of implants to bones for other surgeries as well.

It is desirable to develop a functional implant set that affixes to the bone without adhesives like cement. Furthermore, implants other than for the knee would also benefit from alternative affixation methods rather than adhesives, and such other implants include hip implants, total knee implants of both the femoral and tibial variants, shoulder implants, ankles and knuckles, for example.

SUMMARY

Examples described herein include an implant device and methods for inserting the implant device into bone. An assembly of implant devices may be provided as a set of orthopedic devices or as an orthopedic implant set. An example implant device includes a series of sharp, finned, and/or tapered protrusions that erupt or extend from a bone interfacing surface of the implant device to affix deep into the bone. A method of implantation both compresses cancellous bone tissue, and provides the protrusions as surface structures for future bone ingrowth to more effectively hold the implant device in place. The implant device may be arranged as a tibial and/or femoral implant device including textured, aggressive surfaces which may feature a buildup of rough metal texturing to further increase bone in growth and adhesion. Example methods for insertion of the implant device may use an impactor handle.

In one example, an implant device is described that includes a base having a surface that mates with bone, and a plurality of tapered protrusions positioned on the base and extending from the surface of the base that mates with bone, wherein a surface of the plurality of tapered protrusions includes a textured surface to increase area for bone growth.

In another example, an implant device is described that includes a base having a surface that mates with bone, a plurality of tapered protrusions positioned on the base and extending from the surface of the base that mates with bone, and a peg positioned on the base and extending from the surface of the base that mates with bone. The plurality of tapered protrusions have a height between about 1 mm to about 5 mm, and the peg is positioned between a number of the plurality of tapered protrusions and the peg has a height between about 1 cm to about 3 cm.

In another example, a method for inserting an implant device into bone is described. The insert device includes a base having a surface that mates with bone and a plurality of tapered protrusions positioned on the base and extending from the surface of the base that mates with bone. The method includes forcing the plurality of tapered protrusions of the implant device into the bone, and securing the implant device in place without cement due to the plurality of tapered protrusions cutting into the bone for fixation of the implant device.

Various examples of the apparatus(es) and device(s) described herein may include any of the components, features, and functionalities of any of the other examples of the apparatus(es) and device(s) described herein in any combination.

Various examples of the method(s) described herein may include any of the components, features, and functionalities of any of the other examples of the method(s) described herein in any combination.

The features, functions, and advantages that have been discussed can be achieved independently in various examples or may be combined in yet other examples further details of which can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 5 illustrates a side view of the tapered protrusion, according to an example implementation.

FIG. 6 illustrates an end view of the tapered protrusion, according to an example implementation.

FIG. 7 illustrates a perspective view of the tapered protrusion, according to an example implementation.

FIG. 8 illustrates a top view of the tapered protrusion, according to an example implementation.

FIG. 9 illustrates an end view of another example of the tapered protrusion, according to an example implementation.

FIG. 10 illustrates an end view of another example of the tapered protrusion, according to an example implementation.

FIG. 11 illustrates an end view of another example of the tapered protrusion, according to an example implementation.

FIG. 12 illustrates an end view of yet another example of the tapered protrusion, according to an example implementation.

DETAILED DESCRIPTION

Figure 1:
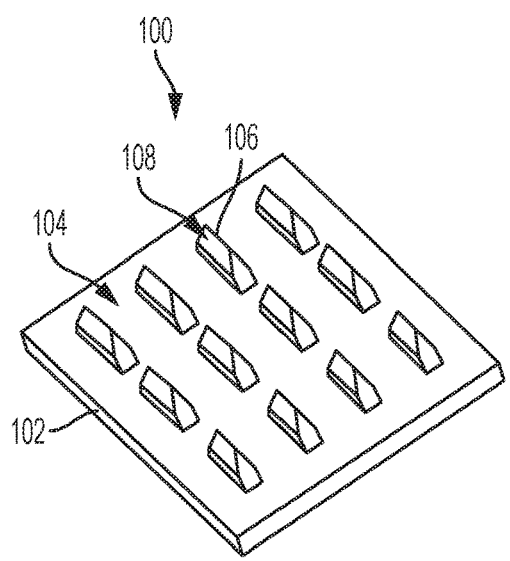
FIG. 1 illustrates an implant device, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

In existing implant devices, cement may be used to fix the device to bone because the device usually has a relatively flat surface. For instance, in knee replacement, surgeons use glue or bone cement to fix the knee implant onto the bone. However, the cement can come loose over time causing problems with fixation of the implant device, and if no cement is used for these types of implants, it is difficult to achieve a tight fit into the bone because the device has the relatively flat surface. Further, flat surfaces with rough texture require intimate contact with living bone to ensure osseointegration or bone ingrowth. A macro-geometry of such implants does not necessarily ensure intimate contact of all such surfaces with living bone.

Within examples described herein, an implant device is described that includes a base with a surface that mates with bone, and a plurality of tapered protrusions positioned on the base and extending from the surface of the base that mates with bone. A surface of the plurality of tapered protrusions includes a textured surface to increase area for the bone to grow onto or into. The tapered protrusions can be arranged in rows and columns that are intended to affix the implant device to a bone of the patient, as well as stimulate long term bone ingrowth into the implant device. The implant device, thus, eliminates a need for bone cement to fix the implant device to the bone. The protrusions ensure that all surfaces of the implant device intended for fixation to the bone achieve this via interference fit of the protrusions into the corresponding bone surfaces. Traditional implants may have a limited number of pegs to assist in initial stability of the implant during cementation or when used with cementless implants designed for bone ingrowth or ongrowth fixation. These typical devices are not intended to provide final implant durable fixation, but instead provide initial alignment and temporary stability. The protrusions described herein are intended to provide both primary and secondary long-term fixation of the implant by the nature of their large overall surface area and plurality of protrusions included on the implant, for example.

The tapered protrusions or fin-like structures are positioned on an inner geometry of the implant device, and the tapered protrusions dig into bone to achieve a rigid fixation and total contact of the implant device with bone. If any gaps remain between the implant device and the bone, or between the tapered protrusions and the bone, bone heals and grows to the tapered protrusions for dependable rigid fixation that is durable.

Examples below also describe methods for fixing implant devices to bone that utilize the structure of the implant device for fixation rather than using bone cement. In an example method of use, bone may be pre-cut with openings, and the implant device is hammered into the bone in which the tapered protrusions are slightly larger than the pre-cut openings so as to become rigidly fixed into the bone. Subsequently, bone in-growth is encouraged when bone is stressed, and bone can grow into any gaps or areas around the tapered protrusions. Thus, the tapered protrusions achieve an initial fixation into the bone, and provide for an area for bone to grow due to the textured surfaces of the protrusions.

The implant device and tapered protrusions can be used in a number of different geometries that can be applied to various implants throughout the field of orthopedics and generally for any orthopedic joint resurfacing and/or replacement. Thus, within some examples, the implant device (and/or base of the implant device) may take the form of a hip implant device, a thumb implant device, a shoulder implant device, a cementless unicompartmental knee replacement (UKA) implant, femoral implant device, a tibia implant device, a pelvis implant device, or others.

Referring now to the figures, FIG. 1 illustrates an implant device 100, according to an example implementation. The implant device 100 includes a base 102 having a surface 104 that mates with bone, and a plurality of tapered protrusions 106 positioned on the base 102 and extending from the surface 104 of the base 102 that mates with bone. A surface 108 of the plurality of tapered protrusions 106 includes a textured or porous surface to increase area for bone growth.

The implant device 100 may be one integral component, and thus, the base 102 and the plurality of tapered protrusions 106 may be manufactured as one piece. As examples, the implant device 100 may be manufactured by using any number of techniques such as casting, forging, machining, or additive manufacturing. The implant device 100 including the base 102 and the plurality of tapered protrusions 106 may be made using a metal, such as a titanium or cobalt, or alloys thereof.

The base 102 is shown as a square, and the example implant device 100 shown in FIG. 1 may be used for a tibia implant. However, the base 102 may be formed in other geometries as needed for other implant scenarios.

The surface 104 of the base 102 may also include a textured surface, similar to the surface 108 of the plurality of tapered protrusions 106. As an example, the surface 104 of the base 102 and/or the surface 108 of the plurality of tapered protrusions 106 may be a porous/rough inner surface, or can include a coating to achieve a rough/textured surface. Thus, the tapered protrusions 106 can be a porous structure or textured structure. Example types of textured surfaces include a sintered surface, a bead blasted surface, and/or a thermal/plasma sprayed surface. If the implant is additively manufactured, the rough/textured or porous surface can be created during the same manufacturing process and using the same material as the base 102 and the tapered protrusions 106, for example. In one example, the textured or porous surface of the tapered protrusion 106 and/or of the base 102 may include a beaded, sintered cobalt-chrome coating on a cobalt chrome substrate with bead sizes ranging from about 0.007 in to about 0.017 in 0.18 mm to 0.43 mm). In another example, the textured or porous surface of the tapered protrusion 106 and/or of the base 102 may include a beaded, vacuum-sintered titanium coating on a titanium substrate with bead sizes ranging from about 0.007 in to about 0.020 in (0.18 mm to 0.50 mm). In still another example, the textured or porous surface of the tapered protrusion 106 and/or of the base 102 may include vacuum-sintered titanium fiber mesh pads on a titanium substrate with a grain size ranging from about 0.01 in to about 0.07 in.

The textured or porous surfaces of the base 102 and/or the plurality of tapered protrusions 106 provide areas for bone growth after inserted into bone. In contrast to smooth surfaces, textured or porous surfaces will create gaps between the plurality of tapered protrusions 106 and the bone during insertion, and bone may grow into the gaps and contact the tapered protrusions 106 over time causing a very rigid and tight fit of the implant device 100 into the bone.

The implant device 100 thus is a unique design that can be attached and fixed into bone without using cement, and is designed to encourage bone growth, while also creating a rigid initial fixation to prevent movement.

Figure 2:
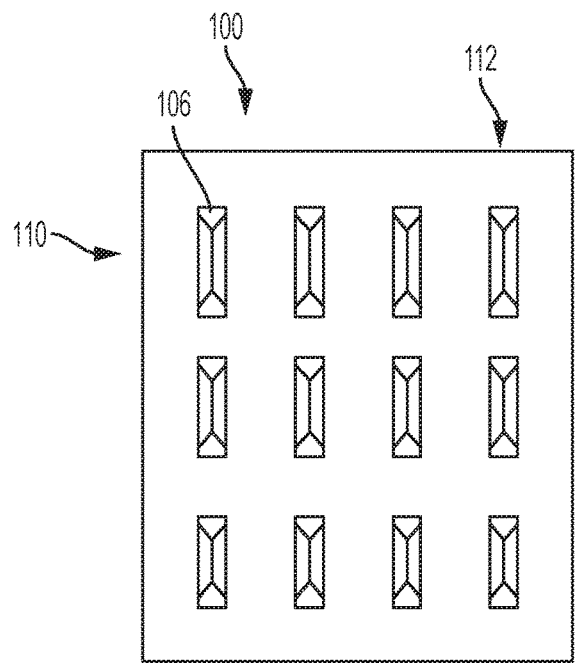
FIG. 2 illustrates a top view of the implant device shown in FIG. 1, according to an example implementation.

FIG. 2 illustrates a top view of the implant device 100, according to an example implementation. In FIG. 2, the plurality of tapered protrusions 106 are arranged in rows and columns, such as row 110 and column 112. The row/column layout spreads the plurality of tapered protrusions 106 over an entirety of the surface 104 of the base 102, for example. In addition, the implant device 100 is illustrated to include twelve tapered protrusions 106 arranged in a three by four array. A number and arrangement of the plurality of tapered protrusions 106 included on the base 102 can depend on spacing between individual protrusions. In an example, the plurality of tapered protrusions 106 are arranged on the base 102 spaced apart by about 2 mm to about 10 mm. Further, although the plurality of tapered protrusions 106 are shown in straight rows/columns, the plurality of tapered protrusions 106 can be arranged in various layouts including curved rows, for example.

Figure 3:
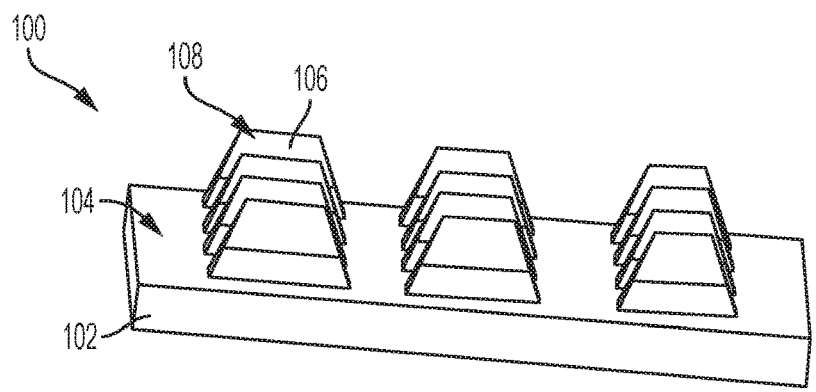
FIG. 3 illustrates a side view of the implant device shown in FIG. 1, according to an example implementation.
Figure 4:
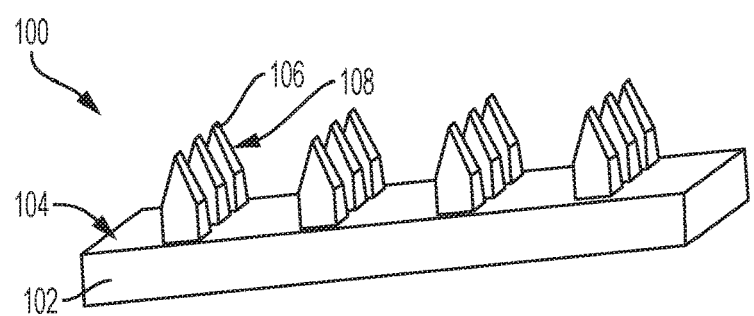
FIG. 4 illustrates an end of the implant device shown in FIG. 1, according to an example implementation.

FIG. 3 illustrates a side view of the implant device 100, according to an example implementation. FIG. 4 illustrates an end of the implant device 100, according to an example implementation.

Within FIGS. 1-4, the implant device is illustrated to include twelve tapered protrusions. However, the implant device 100 may include more or fewer tapered protrusions 106 as well, and/or the tapered protrusions 106 may be arranged in different geometric layouts as well depending on a number of factors. Example factors include a type of implant, a size of the plurality of tapered protrusions 106, a spacing between the plurality of tapered protrusions 106, a layout of the tapered protrusions 106 on the base 102, and a size of the base 102, for example. Each factor is further described below.

The plurality of tapered protrusions 106 can be arranged to cover a certain percentage of the surface 104 of the base 102 to provide additional surface area for the implant device 100 to mate with bone. Example percentages can include 20%, 25%, 50%, or up to 75% of the surface 104 of the base 102. Alternatively, a minimum and maximum number of tapered protrusions can be set for the implant device 100, depending on a type of implant for use of the implant device and a size of the base 102. In some examples, it may be desirable to include as many tapered protrusions as needed to at least double a surface area of the implant device 100.

Thus, the implant device 100 can be configured in a variety of ways to include a variety of number of tapered protrusions, each of which may have varying heights, lengths, widths, spacing between each other, and/or different layouts or patterns as well. A shape, size, placement/pattern, and number of tapered protrusion can be determined based on the use of the implant device 100 as a specific implant (e.g., tibia implant device, shoulder implant device, etc.). In addition, the size, shape, height, length, and width of the tapered protrusions 106 may vary among each other on the implant device 100 so that some tapered protrusions 106 are shorter, wider, etc., than others on the implant device 100, as shown and described in more detail below.

In the example implant device 100 shown in FIGS. 1-4, the implant device 100 is symmetric in that the plurality of tapered protrusions 106 are arranged symmetrically on the surface 104 of the base 102.

FIGS. 5-8 illustrate an example of the tapered protrusion 106, as shown on the implant device 100 in FIGS. 1-4. FIG. 5 illustrates a side view of the tapered protrusion 106, according to an example implementation. FIG. 6 illustrates an end view of the tapered protrusion 106, according to an example implementation. FIG. 7 illustrates a perspective view of the tapered protrusion 106, according to an example implementation. FIG. 8 illustrates a top view of the tapered protrusion 106, according to an example implementation. Note that the illustrations in FIGS. 5-8, and throughout all figures of the description, are not necessarily drawn to scale.

The tapered protrusion 106 may have a height between about 1 mm to about 5 mm, a length between about 2 mm to about 4 cm, and a width between about 0.5 mm to about 2.5 mm. Ranges of the height, length, and width can also vary in size, and as used herein, the term "about" may refer to +/−0.25 mm. In one example, the tapered protrusion 106 is 5 mm in height, 5 mm in length, and 2 mm in width for the layout and arrangement as shown in FIG. 1. Other examples are possible as well.

In further examples, the tapered protrusion 106 may be greater than about 2 mm but less than about 8 mm in length. In still other examples, the tapered protrusion 106 may be greater than about 2 mm and less than about 4 cm in length. Many variations in size of the tapered protrusion 106 can be used, and sizes and ranges of sizes described herein are some examples. The tapered protrusion 106 is shown in FIG. 5 to generally have a trapezoidal shape.

FIG. 6 illustrates that the tapered protrusion 106 includes a bottom portion 114 with approximately parallel side walls 116 and 118, and a top portion 120 connected to the bottom portion 120. The bottom portion 114 may be generally rectangular, and a thickness of the bottom portion 114 can be between about 0.5 mm to about 2.5 mm. The top portion 120 may be generally triangular (and/or pyramidal as shown and described below with reference to FIG. 8), and the top portion 120 has side walls 122 and 124 that slant inward and connect at a tapered tip 126. For example, the side walls 122 and 124 may slant inward at an angle of up to about 45° to create the tapered tip 126 having a pointed tip. The tapered tip 126 allows the tapered protrusion 106 to cut into bone in a direction of bone insertion, for example. In some examples, the tapered tip 126 is not necessarily sharp, and could be slightly filleted and/or truncated to have a broader apex. For example, small fillets can be cast on the sharp tip corners for ease of manufacturability.

As shown in FIG. 6, the tapered protrusion 106 includes the side walls 122 and 124 that slant inward and gradually narrow to the tapered tip 126. This reduces a thickness of the tapered protrusion 106 from the bottom portion 114 toward the tapered tip 126 to enable the tapered tip 126 and the side walls 122 and 124 to become cutting surfaces.

FIG. 7 illustrates the tapered protrusion 106 with the bottom portion 114 having ends 128 and 130 connected to the parallel side walls 116 and 118 (side wall 118 is not shown and is the back facing wall in FIG. 7), and the ends 128 and 130 slant inward toward the tapered tip 126. In one example, the ends 128 and 130 may slant inward at an angle up to about 45°. The top portion 120 also has ends 132 and 134 each slanted inward toward the tapered tip 126, and an angle of slant of the ends 132 and 134 may match that as the angle of slant of the ends 128 and 130, for example. This creates an example pyramidal configuration.

In one example, the tapered protrusion 106 may be in a form of trapezoidal blades or arranged as trapezoidal blades. For example, the tapered protrusion 106 has a pointed tip to enable cutting into the bone, and thus, side walls of the bottom portion 114 and/or of the top portion 120 may be slanted inward to form the pointed tip.

FIG. 8 further illustrates an example of the pyramidal configuration from a top view. In addition, as shown in FIG. 8, the tapered protrusion 106 has the tapered tip 126 formed as a cutting edge that aligns with a direction of bone insertion. Thus, the plurality of tapered protrusions 106 (as shown in FIG. 1) can be oriented on the base 102 in an alignment with the direction of bone insertion to increase effectiveness of cutting into the bone.

FIG. 9 illustrates an end view of another example of the tapered protrusion 106, according to an example implementation. In FIG. 9, the side walls 116 and 118 on the bottom portion 114 taper inward as well toward the tapered tip 126. Within examples, the side walls 116 and 118 may taper inward up to about 20°.

FIG. 10 illustrates an end view of another example of the tapered protrusion 106, according to an example implementation. In FIG. 10, the side walls 122 and 124 on the top portion 120 have a curved sloping surface. Thus, the side walls 122 and 124 on the top portion 120 may form concave sides. In addition, the tapered tip 126 may be a flat tip as shown in FIG. 10. The tapered protrusion 106 in FIG. 10 gradually narrows from a base to the tapered tip 126, and in some examples, a width of the tapered tip 126 is less than 0.5 mm.

FIG. 11 illustrates an end view of another example of the tapered protrusion 106, according to an example implementation. In FIG. 11, the side walls 122 and 124 on the top portion 120 have a curved sloping surface, and the tapered tip 126 is a pointed tip.

FIG. 12 illustrates an end view of yet another example of the tapered protrusion 106, according to an example implementation. In FIG. 12, the side walls 122 and 124 on the top portion 120 have even further inward sloping surfaces as compared to that shown in FIG. 11, and the tapered tip 126 is a pointed tip.

Although the examples shown in FIGS. 9-12 illustrate sharp edges and transitions, rounded edges and transitions between features may be used as well.

Figure 13:
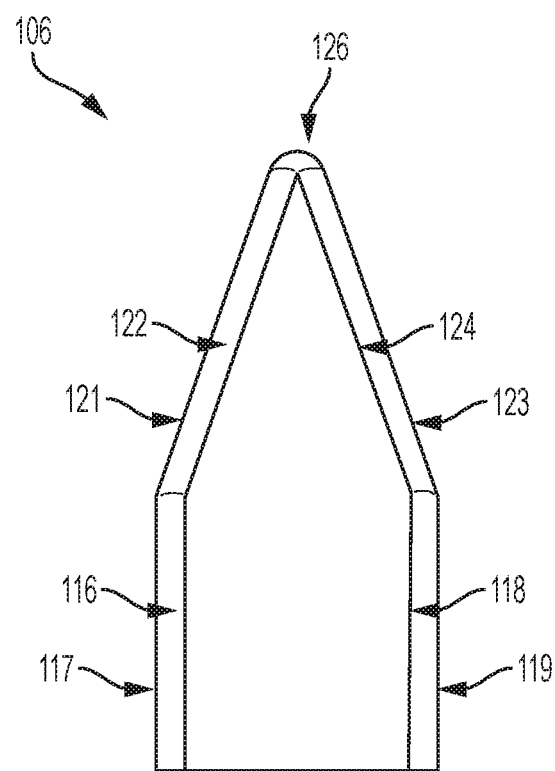
FIG. 13 illustrates a front view of yet another example of the tapered protrusion, according to an example implementation.

FIG. 13 illustrates a front view of yet another example of the tapered protrusion 106, according to an example implementation. In FIG. 13, the side walls 116, 118, 122, and 124 each have fillets 117, 119, 121, and 123, respectively, on the edges. In addition, the tapered tip 126 includes a filleted tip.

Figure 14:
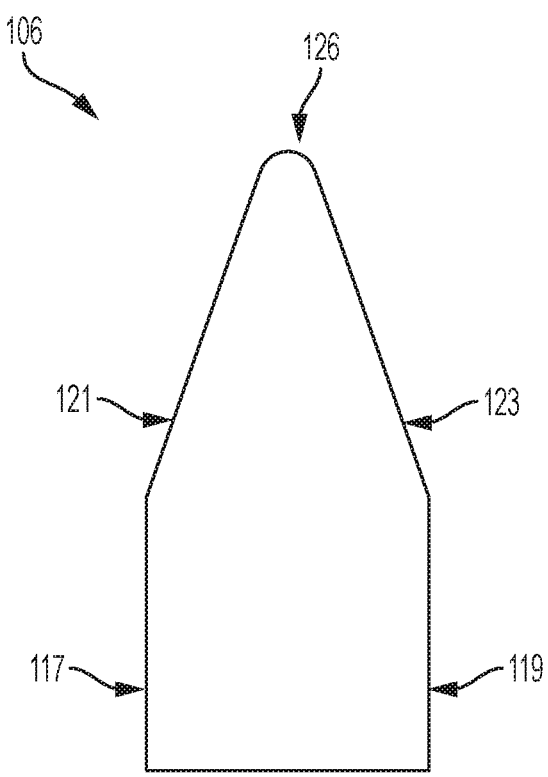
FIG. 14 illustrates an alternative front view of the tapered protrusion of FIG. 13, according to an example implementation.

FIG. 14 illustrates an alternative front view of the tapered protrusion 106 of FIG. 13, according to an example implementation. In FIG. 14, the fillets 117, 119, 121, and 123 are included on the side walls.

Within the examples shown in FIGS. 9-14, it can be seen that the tapered protrusion 106 may be formed having various sloping features of the side walls of the bottom and top portions, and various geometries of the tapered tip. Any combination of the different sloping or parallel walls and flat or point tips may be used. Within the examples, the side walls 116 and 118 on the bottom portion 114 are symmetrical, and the side walls 122 and 124 on the top portion 120 are symmetrical.

As described above, the implant device 100 including the tapered protrusions 106 may be arranged in different geometric layouts depending on a number of factors. In addition, the tapered protrusions 106 may be formed in a number of varieties as shown in FIGS. 9-14.

As further variations, the plurality of tapered protrusions 106 may also vary in density and/or porosity. For example, the textured or porous surface 108 of the tapered protrusion 106 can include a porous coating, a sintered surface, a bead blasted surface, a thermal/plasma spray. As another example, the plurality of tapered protrusions 106 can vary in porosity such that the bottom portion 114 is more porous than the top portion 120. This can be accomplished by selectively varying porosity using additive manufacturing. In one example, a volume percentage of porosity may vary between about 30%-70% between the bottom portion 114 and the top portion 120.

Using variable porosity in the tapered protrusion 106 enables the porosity of the tapered protrusion to more closely match that of the native bone into which it interfaces at various depths, for example. The tapered protrusion 106 may be less porous at the top portion 120 that is inserted deeper into bone, for example.

Figure 15:
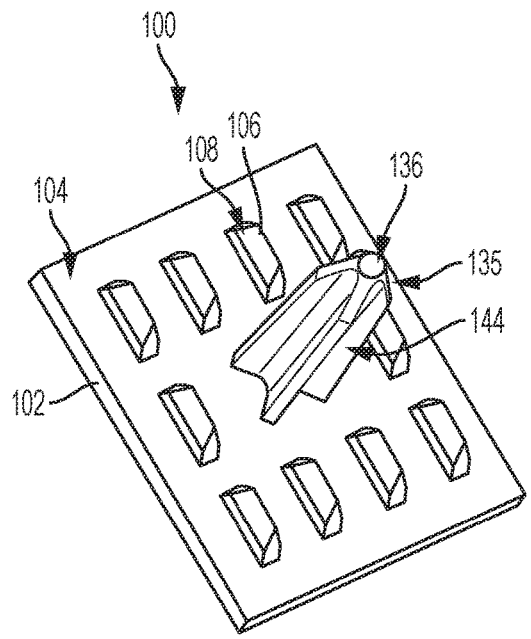
FIG. 15 illustrates another example of the implant device, according to an example implementation.

FIG. 15 illustrates another example of the implant device 100, according to an example implementation. In FIG. 15, the implant device 100 includes the base 102 having the surface 104 that mates with bone, and the plurality of tapered protrusions 106 positioned on the base 102 and extending from the surface 104 of the base 102 that mates with bone. The implant device 100 also includes a peg 135 positioned on the base 102 and extending from the surface 104 of the base 102 that mates with bone. The peg 135 is positioned between a number of the plurality of tapered protrusions 106. As shown, the peg 135 is positioned in a center of the base 102, or in a center row and center column of a layout of the plurality of tapered protrusions 106. The peg 135 is positioned on the base 102 such that a single tapered protrusion is positioned on the base 102 at both sides of the peg 135, and two tapered protrusions are positioned on the base 102 at both ends of the peg 135. The single tapered protrusion positioned on the base 102 at the sides of the peg 135 is positioned lengthwise next to the peg 135, and the peg 135 may have a length about equal to a length of the tapered protrusion as shown in FIG. 15. The two tapered protrusions positioned on the base 102 at both ends of the peg 135 are positioned to be spaced apart a distance that is about equal to a width of the peg 135, for example.

Thus, as shown in FIG. 15, the implant device 100 has two interior tapered protrusions removed and the peg 135 is positioned on the base 102 at the interior position. The implant device 100 in FIG. 15 includes the central peg 135, and ten tapered protrusions.

The peg 135 is shown with a flat tip 136. However, in other examples, the peg 135 may include a sharp tip.

In the example shown in FIG. 15, the plurality of tapered protrusions 106 have a height between about 1 mm to about 5 mm, and the peg 135 has a height between about 1 cm to about 3 cm. In some examples, the peg 135 may be about five to ten times the height of the tapered protrusion 106 so as to extend deeper into the bone.

In addition, in the example shown in FIG. 15, the plurality of tapered protrusions 106 are arranged along a peripheral of the base 102, and surrounding the peg 135.

Figure 16:
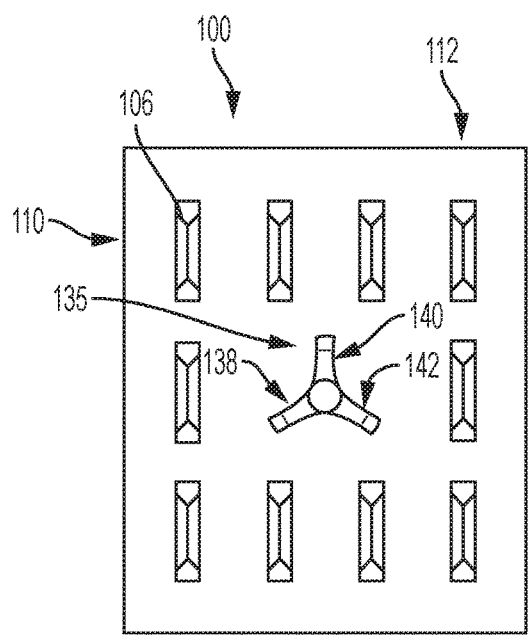
FIG. 16 is a top view of the implant device of FIG. 15, according to an example implementation.

FIG. 16 is a top view of the implant device 100 of FIG. 15, according to an example implementation. In FIG. 16 the peg 135 is shown as a three prong peg and includes prongs 138, 140, and 142. In some examples, a surface 144 of the peg 135 is smooth and the surface 108 of the plurality of tapered protrusions 106 includes a textured surface. In other examples, the surface 144 of the peg 135 also includes a textured or porous surface. In a further example, a textured surface of the peg 135 may be a thinner coating as compared to a textured or porous surface on the tapered protrusions 106, or a textured surface of the peg 135 may not cover an entirety of the peg 135 (i.e., the coating may cover only a bottom portion proximal to the surface 104 of the base 102 from which it protrudes). In any event, the tapered protrusion 106 differentiates from the peg 135 on the implant device 100.

The peg 135 may be useful to provide a deep seating of the implant device 100 into bone, whereas the tapered protrusions 106 provide a more shallow seating of the implant device 100 into bone and encourage bone growth surrounding the tapered protrusions 106 for enhanced long term affixation of the implant device 100 into the bone.

Figure 17:
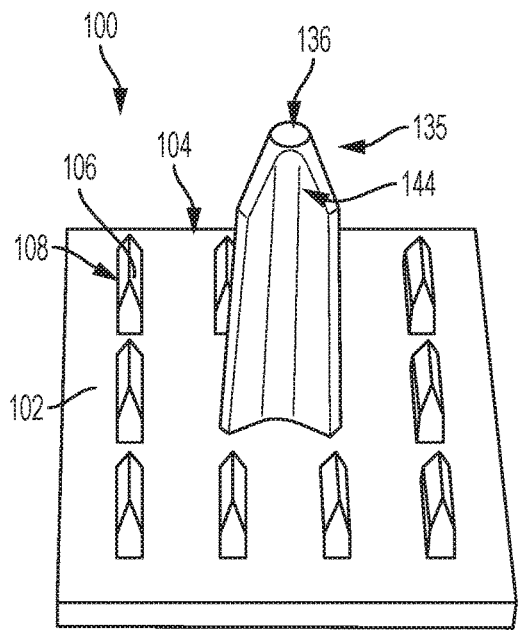
FIG. 17 illustrates another example of the implant device, according to an example implementation.

FIG. 17 illustrates another example of the implant device 100, according to an example implementation. In FIG. 17, the implant device 100 is shown to include a rough textured surface. For example, the surface 104 of the base 102 includes the textured surface, the surface 108 of the plurality of tapered protrusions 106 includes the textured surface, and the surface 144 of the peg 135 includes the textured surface. The textured surface is a rough surface, and may be a porous coating applied. The textured surface enables an increased grip and attachment to the bone, for example, as compared to a smooth surface.

Figure 18:
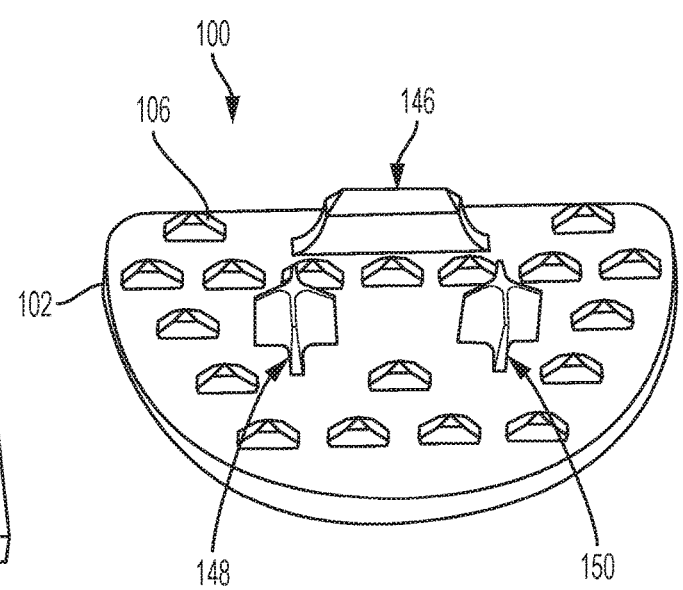
FIG. 18 illustrates another example of the implant device, according to an example implementation.

FIG. 18 illustrates another example of the implant device 100, according to an example implementation. In FIG. 18, the implant device 100 is shown to include the plurality of tapered protrusions 106 in a different layout, namely, in five rows and the tapered protrusions 106 are separated by three pegs 146, 148, and 150. The base 102 is configured similar to a half-moon shape, and the peg 146 is positioned proximal to a straight edge of the base 102 with two tapered protrusions on either side of the peg 146. Then, proceeding down toward the curved portion of the base 102, next is a row of seven tapered protrusions. Following, the two pegs 148 and 150 are positioned about mid-way down the base 102, and a single tapered protrusion is positioned at edges of the base 102 next to the pegs 148 and 150. No tapered protrusion is positioned directly between the pegs 148 and 150. Then, a row of three tapered protrusions follows, and finally a row of four tapered protrusions is positioned proximal the curved edge of the base 102.

In the example shown in FIG. 18, the plurality of tapered protrusions 106 are arranged along a peripheral of the base 102, and surrounding the pegs 148 and 150.

Figure 19:
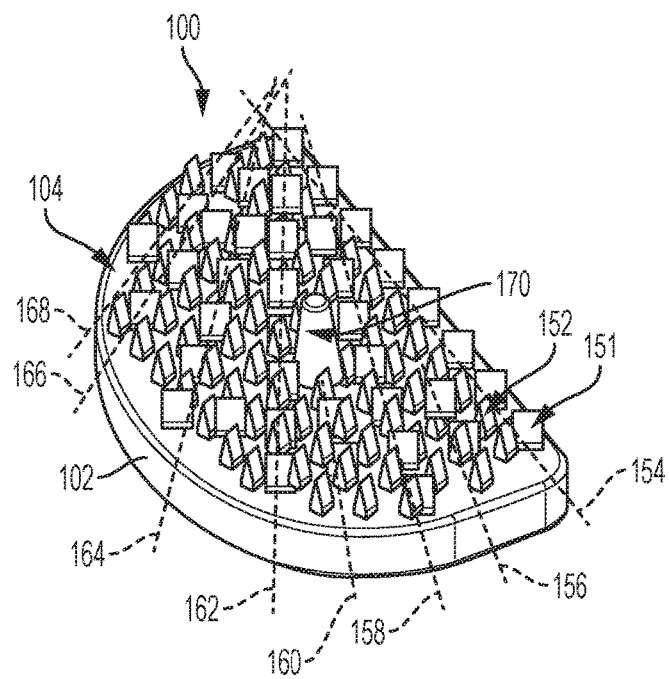
FIG. 19 illustrates another example of the implant device, according to an example implementation.

FIG. 19 illustrates another example of the implant device 100, according to an example implementation. In FIG. 19, the implant device 100 is shown to include the plurality of tapered protrusions in a different layout, namely, by alternatively an alignment of the tapered protrusions on the base 102. For example, a first alignment is shown by tapered protrusion 151 in which the tapered protrusion is angled at about 45° with respect to an edge of the base 102. A second alignment is shown by tapered protrusion 152 in which the tapered protrusion is angled in an opposite direction to that of the angle of tapered protrusion 151, and also at about 45° with respect to an edge of the base 102. The implant device 100 of FIG. 17 includes rows of tapered protrusions alternatively between the alignment of tapered protrusion 151 and the alignment of tapered protrusion 152. Rows of tapered protrusions angled as the tapered protrusion 151 can be seen as rows 154, 156, 158, 160, 162, 164, 166, and 168. Rows of tapered protrusions angled as the tapered protrusion 152 are positioned between the rows 154, 156, 158, 160, 162, 164, 166, and 168.

The tapered protrusions shown in the implant device 100 of FIG. 19 may be the same or substantially the same as any of those described in FIGS. 5-14, for example.

Furthermore, the implant device 100 in FIG. 19 includes a central peg 170, and additional tapered protrusions may be positioned in open spaces between the rows 154, 156, 158, 160, 162, 164, 166, and 168. Thus, the implant device 100 in FIG. 19 has a dense arrangement of tapered protrusions surrounding the central peg 170. In addition, the surface 104 of the base 102 and/or a surface of any of the tapered protrusions in the implant device in FIG. 17 may be smooth or a textured surface, for example.

Figure 20:
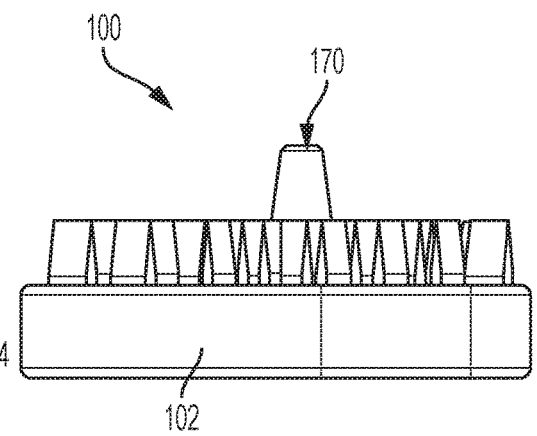
FIG. 20 is a side view of the implant device shown in FIG. 19, according to an example implementation.

FIG. 20 is a side view of the implant device shown in FIG. 19, according to an example implementation. The central peg 170 is shown to have a height that is about twice the height as the tapered protrusions, in this example. The central peg 170 is also shown with a flat tip, however, the central peg 170 may include a sharp tip in other examples.

Figure 21:
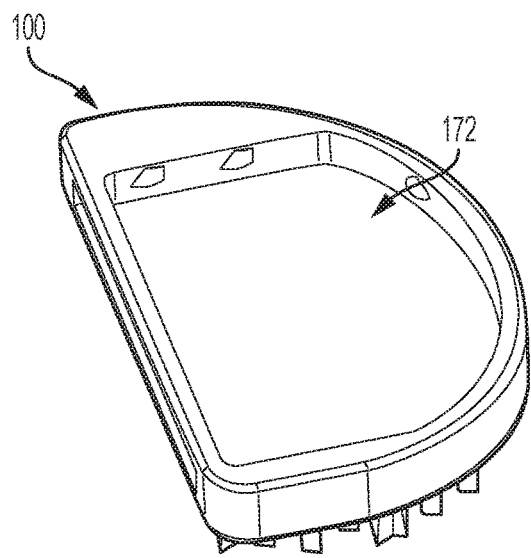
FIG. 21 is a bottom perspective view of the implant device shown in FIG. 19, according to an example implementation.
Figure 22:
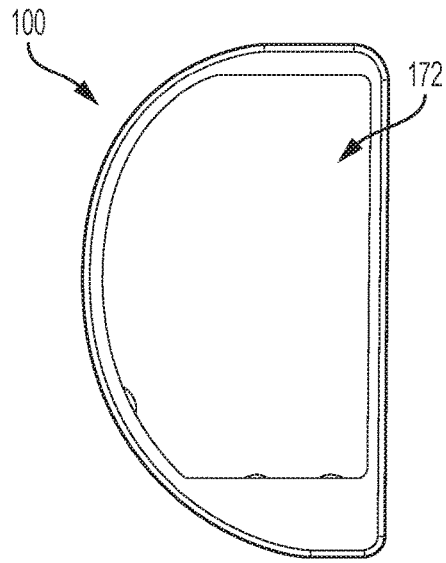
FIG. 22 is a bottom view of the implant device shown in FIG. 19, according to an example implementation.

FIG. 21 is a bottom perspective view of the implant device shown in FIG. 19, according to an example implementation. FIG. 22 is a bottom view of the implant device shown in FIG. 19, according to an example implementation. As shown in FIGS. 21-22, the implant device 100 includes a cavity 172. The implant device 100 in FIG. 19 may be a tibial baseplate bone implant device, and the cavity 172 is for holding a spacer that abuts a component of the femur or a femoral implant, for example.

Figure 23:
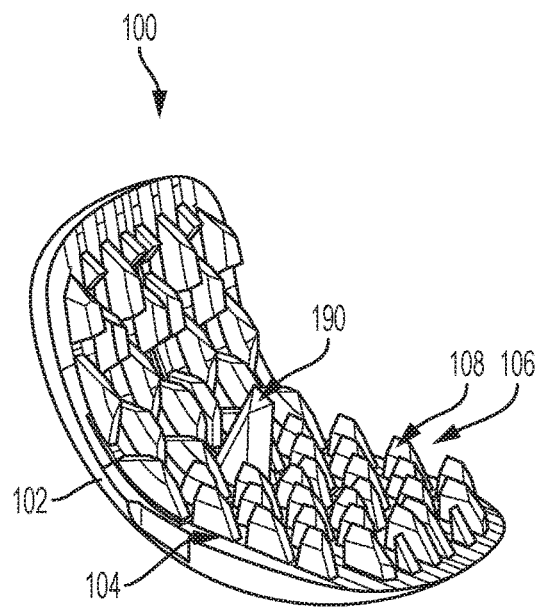
FIG. 23 illustrates another example of the implant device, according to an example implementation.
Figure 24:
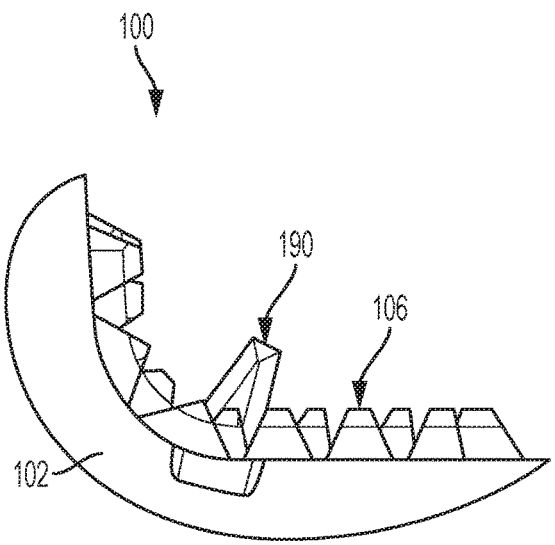
FIG. 24 is a side view of the implant device shown in FIG. 23, according to an example implementation.
Figure 25:
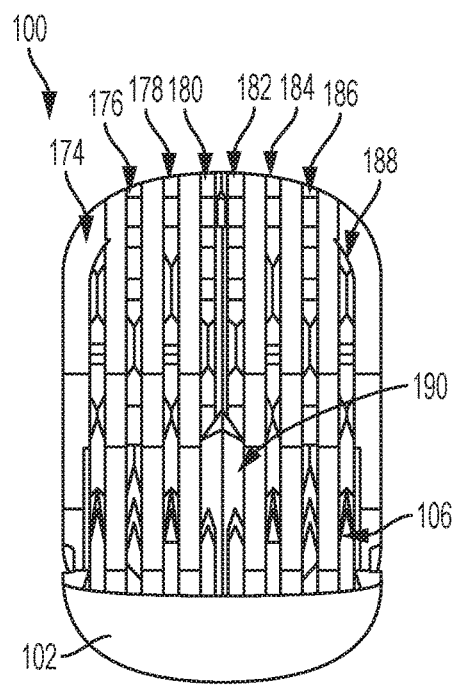
FIG. 25 is a top front-end view of the implant device shown in FIG. 23, according to an example implementation (e.g., showing a posterior edge of the implant device as seen from an anterior approach).
Figure 26:
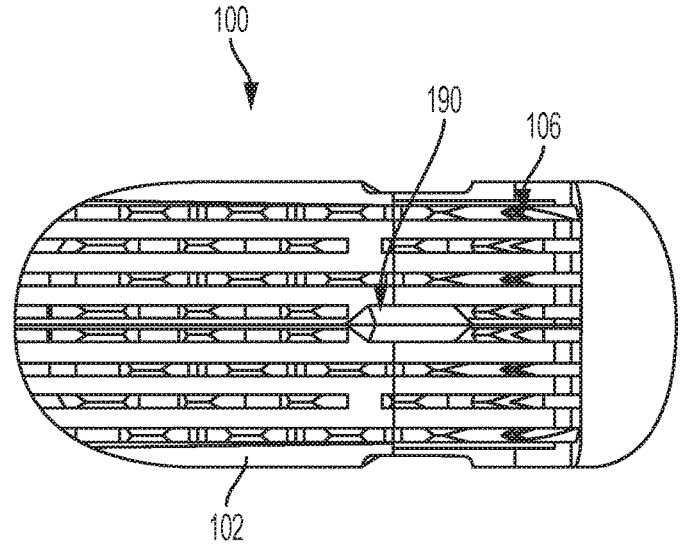
FIG. 26 is a top side view of the implant device shown in FIG. 23, according to an example implementation.

FIG. 23 illustrates another example of the implant device 100, according to an example implementation. FIG. 24 is a side view of the implant device shown in FIG. 23, according to an example implementation. FIG. 25 is a top front-end view of the implant device shown in FIG. 23, according to an example implementation (e.g., showing a posterior edge of the implant device 100 as seen from an anterior approach). FIG. 26 is a top side view of the implant device shown in FIG. 23, according to an example implementation.

In FIGS. 23-26, the implant device 100 is shown to include the base 102 curved, and the plurality of tapered protrusions 106 in a different layout. Namely, the plurality of tapered protrusions 106 are arranged in rows 174, 176, 178, 180, 182, 184, 186, and 188 along a length of the base 102. In addition, the implant device 100 shown in FIGS. 23-26 includes the plurality of tapered protrusions 106 arranged in a variety of sizes. Some are smaller than others, and some are larger than others. The variety of sizes of the plurality of tapered protrusions 106 alternate along the rows 174, 176, 178, 180, 182, 184, 186, and 188, for example. In addition, the variety of sizes of the plurality of tapered protrusions 106 vary due to curvature of the base 102. For example, a length of the plurality of tapered protrusions 106 may be larger a positions on the base 102 with a greater angle of curvature as compared to a length of the plurality of tapered protrusions 106 at ends of the base 102 where there is little or no curvature.

The implant device 100 in FIGS. 23-26 also includes a central peg 190. In FIG. 24, it can be seen that the central peg 190 has a height that is greater than a height of the plurality of tapered protrusions 106. In FIG. 25, it can be seen that the central peg 190 has a width about equal to two rows of the plurality of tapered protrusions 106, for example.

In addition, the surface 104 of the base 102 and/or a surface of any of the tapered protrusions in the implant device in FIGS. 23-26 may be a smooth or a textured or porous surface, for example. Similarly, the surface of the central peg 190 may be a smooth or a textured or porous surface, for example.

Figure 27:
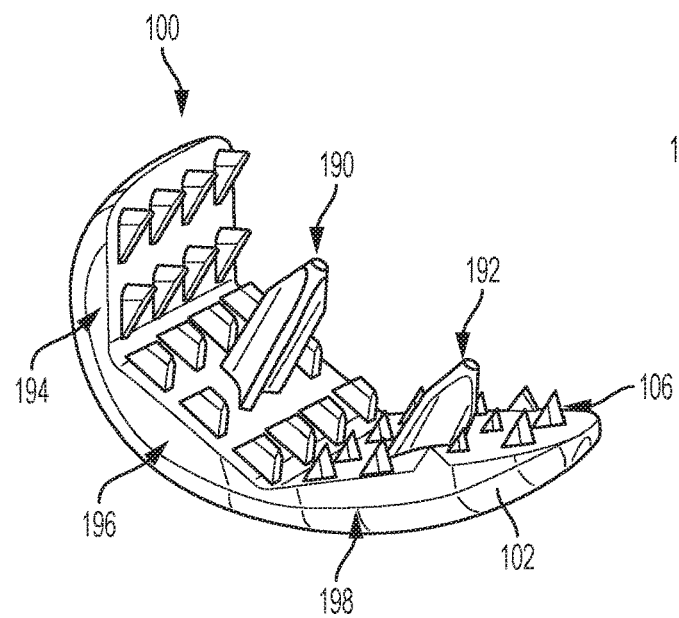
FIG. 27 illustrates another example of the implant device, according to an example implementation.
Figure 28:
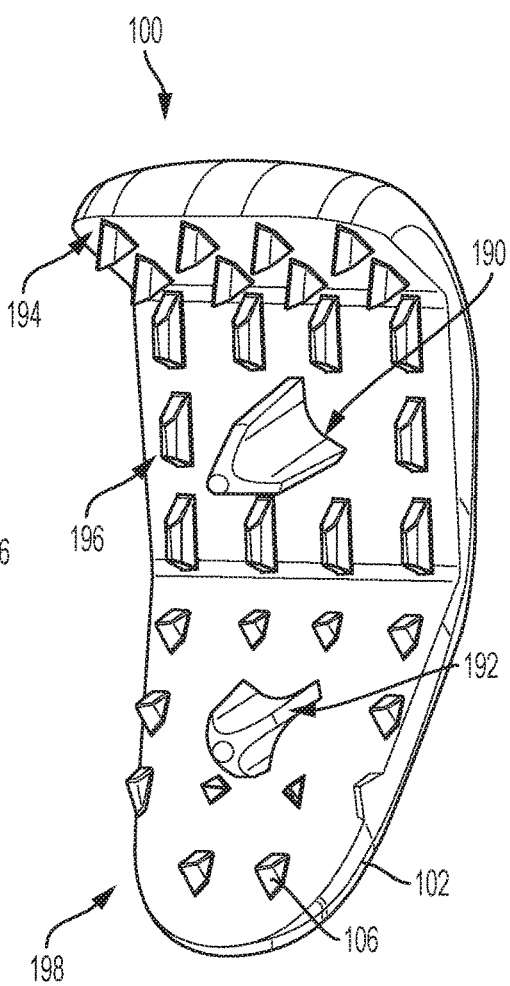
FIG. 28 is another view of the implant device shown in FIG. 27, according to an example implementation.
Figure 29:
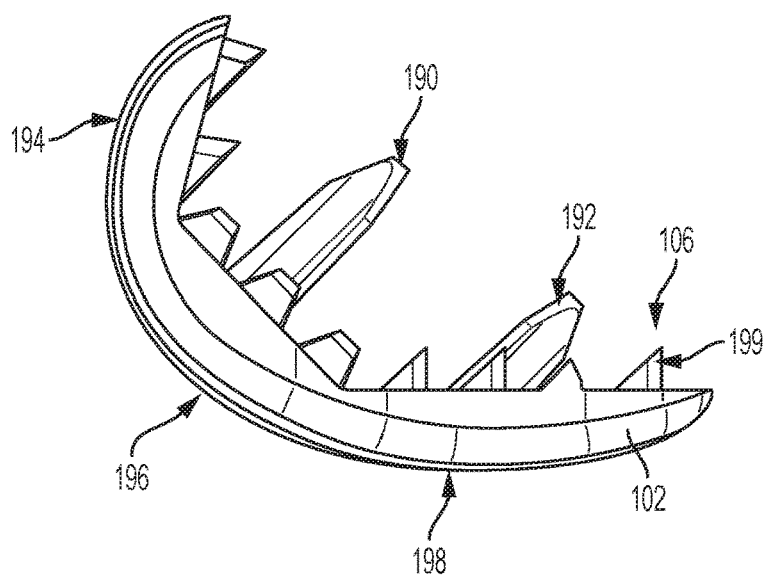
FIG. 29 is a side view of the implant device shown in FIG. 27, according to an example implementation.

FIG. 27 illustrates another example of the implant device 100, according to an example implementation. FIG. 28 is another view of the implant device shown in FIG. 27, according to an example implementation. FIG. 29 is a side view of the implant device shown in FIG. 27, according to an example implementation.

In FIGS. 27-29, the implant device 100 is arranged as a unicompartmental femoral component manufactured with leading edges. The implant device 100 is shown to include the base 102 curved and divided into three sections 194, 196, and 198, and the plurality of tapered protrusions 106 are positioned in a different layout. Namely, the plurality of tapered protrusions 106 are arranged in rows along a length of the base 102. In addition, the implant device 100 shown in FIGS. 27-29 includes the plurality of tapered protrusions 106 arranged in a variety of sizes. Some are smaller than others, and some are larger than others. The variety of sizes of the plurality of tapered protrusions 106 vary among the three section 194, 196, and 198, for example.

The implant device 100 in FIGS. 27-29 also includes the central peg 190 positioned on the section 196, and an anterior peg 192 positioned on the section 198. In FIG. 29, it can be seen that the central peg 190 has a height that is greater than a height of the anterior peg 192. In addition, each of the central peg 190 and the anterior peg 192 has a height that is greater than a height of the plurality of tapered protrusions 106.

In FIGS. 27-29, the tapered protrusions 106 are formed with leading edges, such as leading edge 199. This can be seen in the side view in FIG. 29, for example. The leading edges may be formed as filleted tapered protrusions, as previously described, for example.

Figure 30:
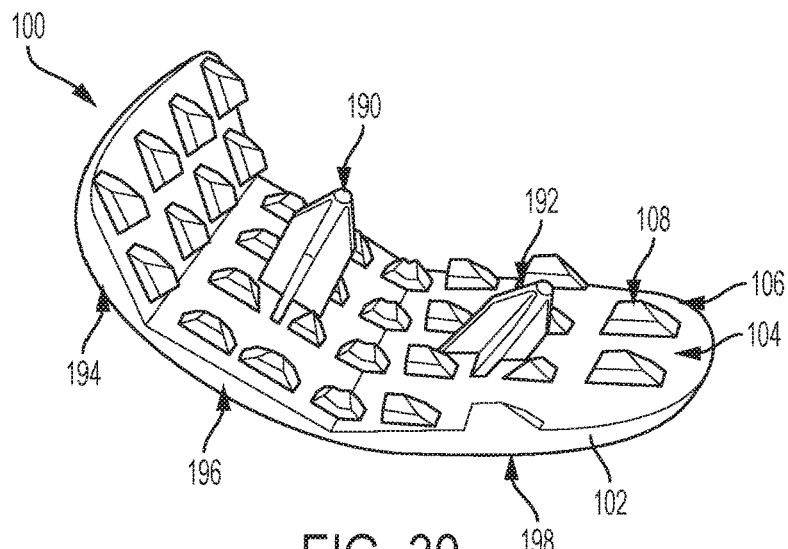
FIG. 30 illustrates another example of the implant device, according to an example implementation.
Figure 31:
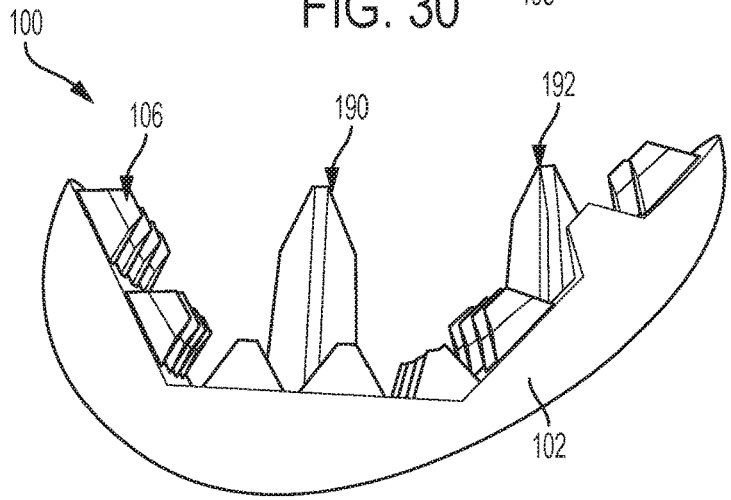
FIG. 31 is a side view of the implant device shown in FIG. 30, according to an example implementation.

FIG. 30 illustrates another example of the implant device 100, according to an example implementation. FIG. 31 is a side view of the implant device shown in FIG. 30, according to an example implementation.

In FIGS. 30-31, the implant device 100 is shown to include the base 102 curved and divided into the three sections 194, 196, and 198, and the plurality of tapered protrusions 106 are positioned in a different layout. Namely, the plurality of tapered protrusions 106 are arranged in four rows along a length of the base 102. In addition, the implant device 100 shown in FIGS. 30-31 includes the plurality of tapered protrusions 106 arranged in a variety of sizes. Some are smaller than others, and some are larger than others. The variety of sizes of the plurality of tapered protrusions 106 vary among the three section 194, 196, and 198, for example.

The implant device 100 in FIGS. 30-31 also includes the central peg 190 positioned on the section 196, and an anterior peg 192 positioned on the section 198. In FIG. 31, it can be seen that the central peg 190 has a height that is greater than a height of the anterior peg 192. In addition, each of the central peg 190 and the anterior peg 192 has a height that is greater than a height of the plurality of tapered protrusions 106.

In FIG. 30, it can be seen that the central peg 190 and the anterior peg 192 have a width that spans about two rows of the plurality of tapered protrusions 106, for example. Each of the central peg 190 and the anterior peg 192 is positioned between four tapered protrusions. The anterior peg 192 is configured to fit on the section 198 level with the central peg 190 even though the section 198 is slanted upward with respect to the section 196.

In addition, the surface 104 of the base 102 and/or a surface of any of the tapered protrusions in the implant device in FIGS. 30-31 may be a smooth or a textured or porous surface, for example. Similarly, the surface of the central peg 190 and/or the anterior peg 192 may be a smooth or a textured or porous surface, for example.

Figure 32:
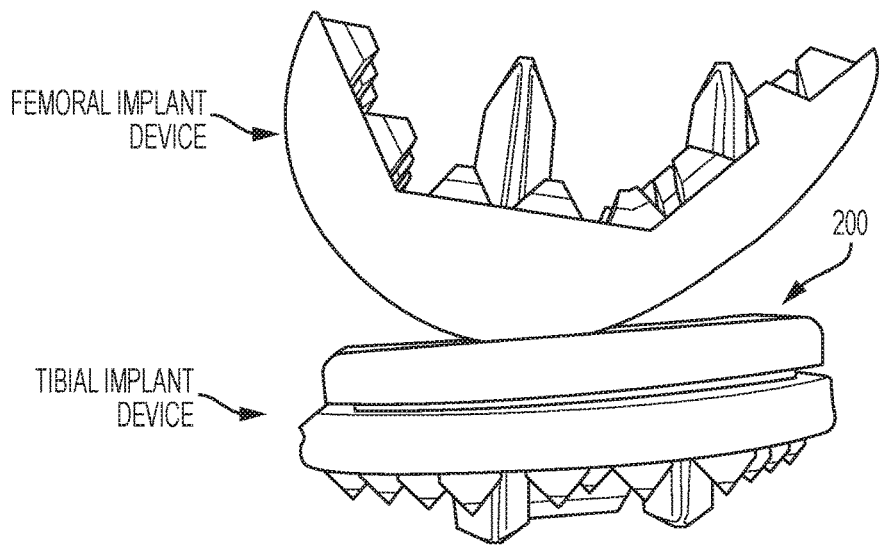
FIG. 32 is a side view of an assembly including the implant device shown in FIG. 18 with the implant device shown in FIGS. 30-31, according to an example implementation.

FIG. 32 is a side view of an assembly including the implant device shown in FIG. 18 with the implant device shown in FIGS. 30-31, according to an example implementation. In this example, the implant device shown in FIGS. 30-31 is a femoral implant device, and the implant device shown in FIG. 18 is a tibial implant device, and tibial insert 200 is provided for the assembly.

Thus, as can be seen in FIGS. 1-4 and FIG. 15-31, the implant device 100 can be arranged to include a variety of configurations of the base including a variety of configurations of tapered protrusions in a variety of layouts with or without a peg or including a variety of pegs. In addition, the implant device 100 may be one integral component, and thus, the base 102, the plurality of tapered protrusions 106, and the peg(s) (if included) may be manufactured as one piece rather than separate components that screw into the base.

A specific arrangement of the implant device depends on an application of use of the implant device. As one example, the implant device shown in FIGS. 1, 15, 18, and 19 may be a tibial baseplate bone implant device. As another example, the implant device shown in FIGS. 23-26 may be a femoral bone implant device. In a further example, multiple implant devices can be arranged as a knee implant assembly, as shown in FIG. 32. In yet further examples, the implant device 100 may be configured as a tibia implant device, a femoral implant device, a unicompartmental knee replacement implant device, a pelvis implant device, a hip implant device, a shoulder implant device, an ankle implant device, and a knuckle implant device for a hand or foot.

Figure 33:
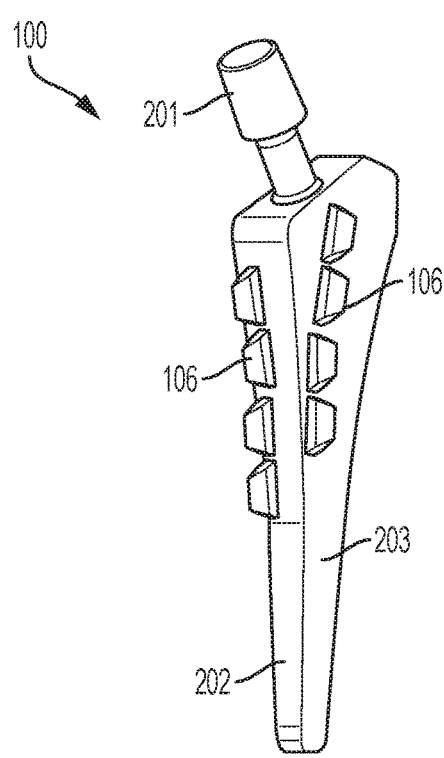
FIG. 33 illustrates another example of the implant device, according to an example implementation.
Figure 34:
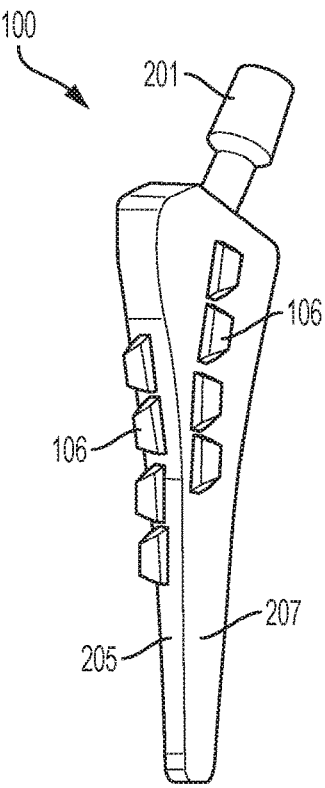
FIG. 34 is another side view of the implant device shown in FIG. 33, according to an example implementation.

FIG. 33 illustrates another example of the implant device 100, according to an example implementation. FIG. 34 is another side view of the implant device shown in FIG. 33, according to an example implementation. In FIGS. 33-34, the implant device 100 is shown as a hip femoral stem component that includes a hip peg insert 201. As shown, the tapered protrusions 106 may be included on any outer surface 202, 203, 205, and 207 of the hip stem that is a bone adhering surface.

Figure 35:
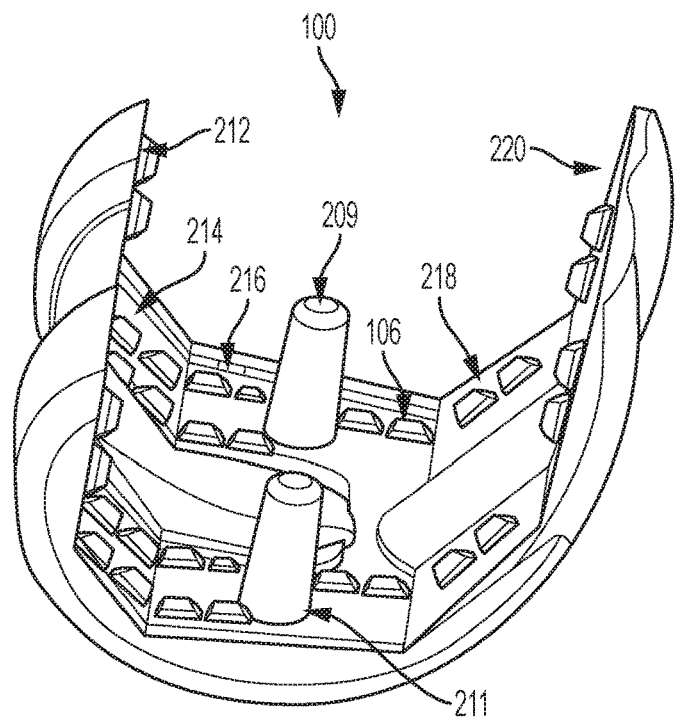
FIG. 35 illustrates another example of the implant device, according to an example implementation.

FIG. 35 illustrates another example of the implant device 100, according to an example implementation. In FIG. 35, the implant device 100 is shown as a total knee femoral component with pegs 209 and 211, and the tapered protrusions 106 are included on any inner surface 212, 214, 216, 218, and 220 of the knee component. Although, the tapered protrusions 106 are shown on every inner surface 212, 214, 216, 218, and 220, the tapered protrusions 106 may be included on only one surface, or only some of the inner surfaces 212, 214, 216, 218, and 220.

Thus, the tapered protrusions 106 may be included on the implant device 100 in various angled configurations as well, depending on an angle of the bone adhering surface to which the tapered protrusions 106 are affixed and protrude from. For example, for the implant device 100 shown in FIG. 1, all of the tapered protrusions 106 extend from the same surface 104, and thus, all of the tapered protrusions are arranged at the same angle with respect to each other. As another example, in FIGS. 23-31, the tapered protrusions 106 shown on the respective implant device extend from various different surfaces that are angled with respect to each other, and thus, the tapered protrusions 106 included on the respective implant device 100 shown in these figures are also arranged at various angles with respect to each other.

In addition, although a number and arrangement of the plurality of tapered protrusions 106 included on the base 102 of the implant device 100 can be variable, within some examples herein, the plurality refers to more than two tapered protrusions. Some existing implant devices include one or two pegs only on the surface of the implant device. However, as described herein, the plurality of tapered protrusions 106 are distinguished from the peg 135, and the implant device 100 at least includes more than two tapered protrusions. The implant device 100 may optionally include the peg 135, as shown in the examples in FIGS. 15-18 (or at least one peg as shown in FIGS. 19-20, FIGS. 23-26), in addition to the plurality of tapered protrusions 106. Further, the implant device 100 may optionally include multiple pegs as shown in the examples in FIG. 18 and FIGS. 27-31, and FIG. 35 in addition to the plurality of tapered protrusions 106. If pegs are included, the pegs are included on the implant device 100 in addition to the plurality of tapered protrusions 106.

Still further, the plurality as used with reference to the tapered protrusions may refer to more than three tapered protrusions, or more than any multiple number of tapered protrusions included on the implant device 100, within various examples.

Figure 36:
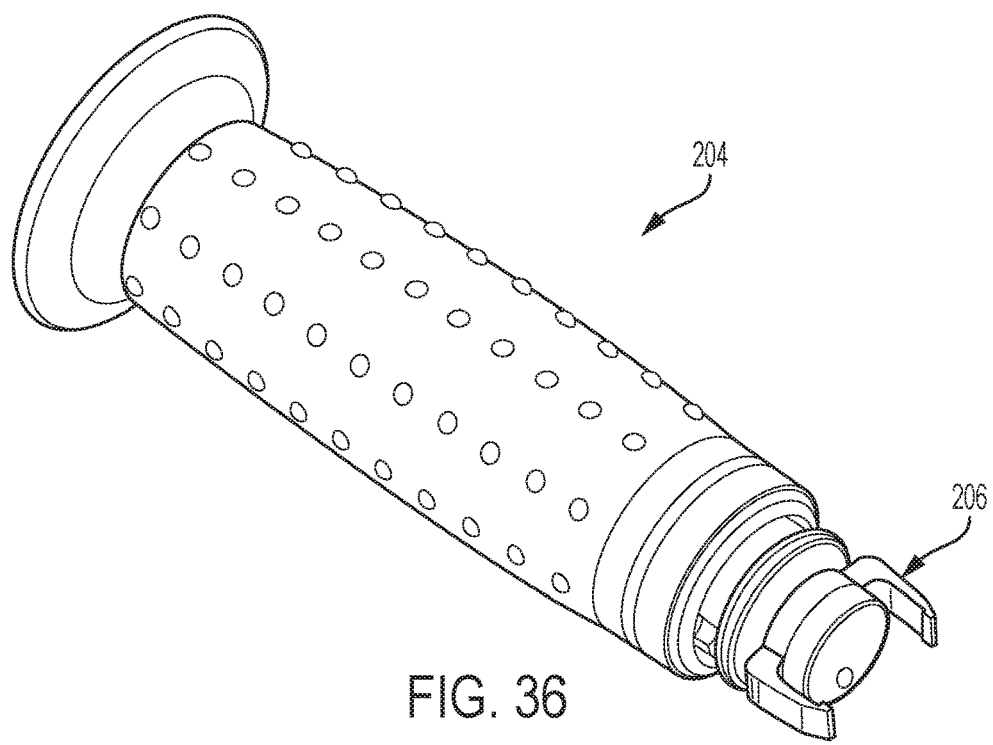
FIG. 36 is an isometric view of the impactor device, according to an example implementation.
Figure 37:
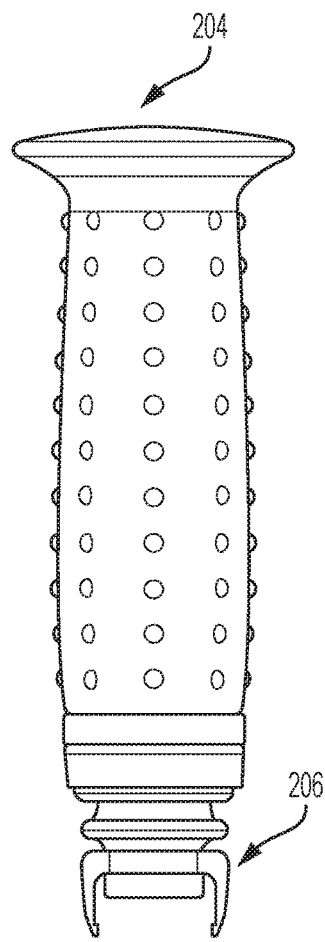
FIG. 37 is a front view of the impactor device shown in FIG. 36, according to an example implementation.
Figure 38:
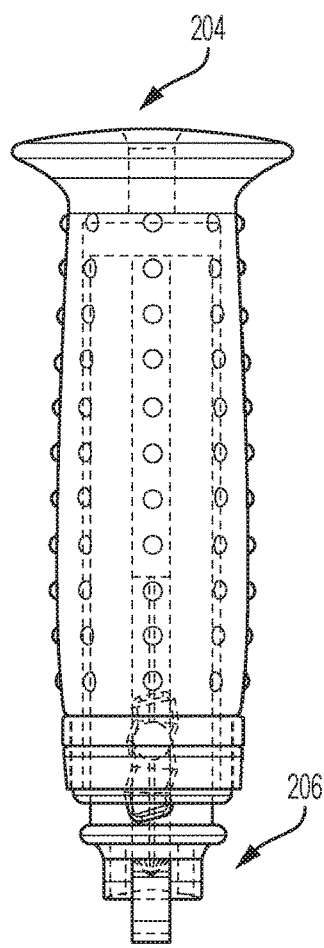
FIG. 38 is a side view of the impactor device shown in FIG. 36, according to an example implementation.
Figure 39:
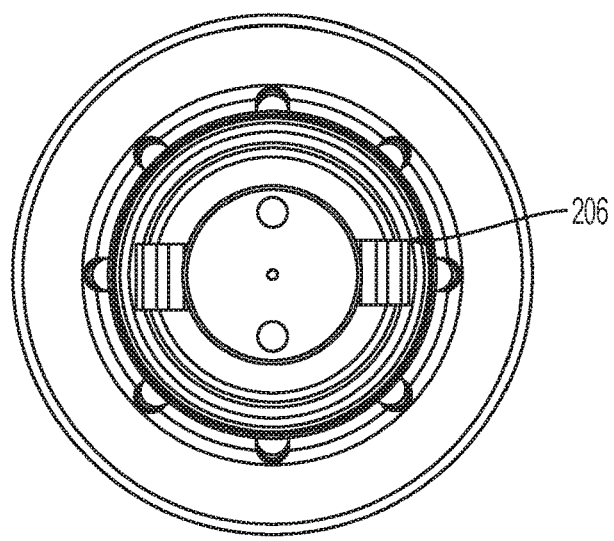
FIG. 39 is a bottom view of the impactor device where the impactor device impacts the implant device into bone, according to an example implementation.
Figure 40:
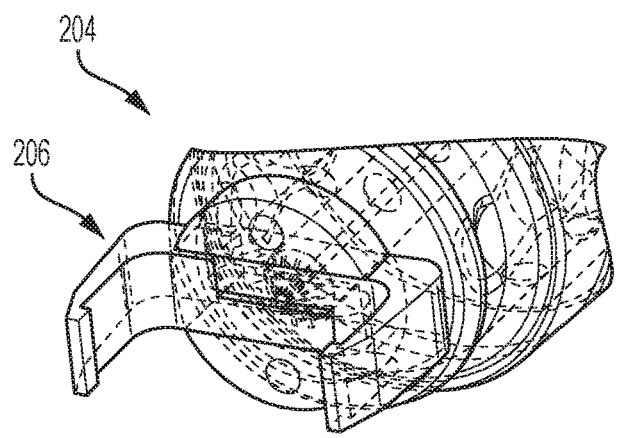
FIG. 40 is a perspective view of a pinion actuated clamp of the impactor device that holds the implant device, according to an example implementation.
Figure 41:
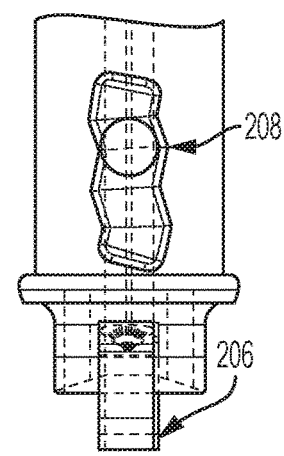
FIG. 41 is a side view of a zig zag channel of the impactor device, according to an example implementation.

FIGS. 36-41 illustrate an example impactor device 204 that may be used for inserting the implant device 100 into bone, according to an example implementation. Specifically, FIG. 36 is an isometric view of the impactor device 204, FIG. 37 is a front view of the impactor device 204, FIG. 38 is a side view of the impactor device 204, according to an example implementation, FIG. 39 is a bottom view of the impactor device 204 where the impactor device 204 impacts the implant device 100 into bone, FIG. 40 is a perspective view of a pinion actuated clamp of the impactor device 204 that holds the implant device 100, and FIG. 41 is a side view of a zig zag channel of the impactor device 204, all according to example implementations.

Figure 42:
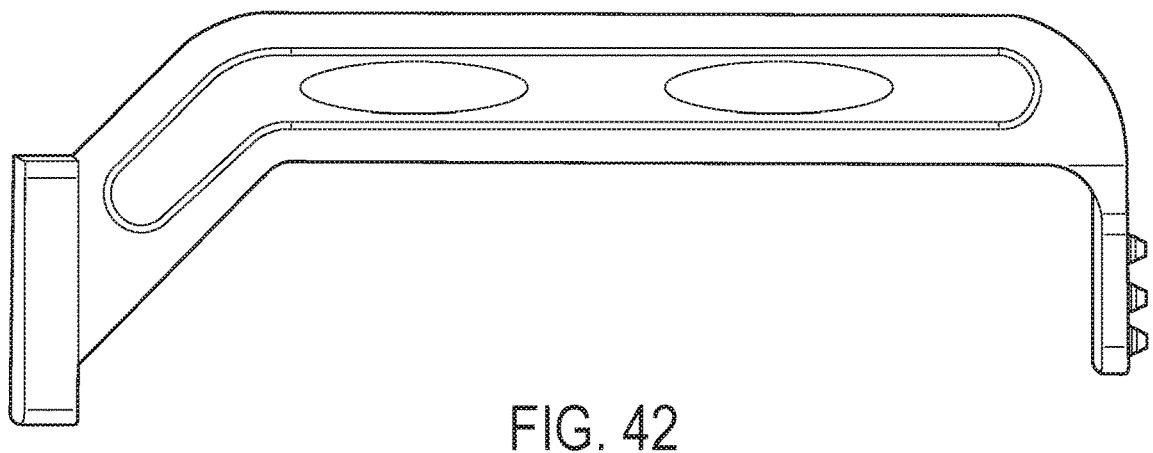
FIG. 42 illustrates an impactor used to pre-punch holes into bone for placement of the implant device, according to an example implementation.

FIG. 42 illustrates an impactor used to pre-punch holes into bone for placement of the implant device 100, according to an example implementation.

As an example method for insertion of the implant device 100 into bone, one implementation considers the implant device assembly shown in FIG. 32. To insert the implant device assembly as shown in FIG. 32, initially, a knee joint of a patient is exposed by a vertical incision that passes through the skin, fat pad, and synovial membrane. Retractors are inserted into the medial and lateral sides of the incision, and the affected joint is exposed. Bone cutting instruments are used to make the needed resections to remove sclerotic and/or arthritic bone. Other anomalous bony growths and related fibrous tissue are also removed as needed.

Once proper surgical preparation has been completed, a size of the implant device is trialed by using a non-implantable reproduction of the implant. This allows the surgeon to test a fit of the implant device, as well as the range of motion of the knee of the patient. After trialing of the knee implant device (prosthesis), the surgeon will have the tibial prosthesis prepared for impaction.

First, a surface of the bone may be machine cut to include slots in the bone that match an orientation of the tapered protrusions 106 of the implant device 100. The slots may be smaller in size than the tapered protrusions 106 so that the tapered protrusions 106 will be driven into the slots for a rigid initial fixation of the implant device 100 to the bone, for example.

The impactor shown in FIG. 42 may be used to pre-punch and precisely cut slots into the bone. For example, for the flat tibial baseplate component, small slots can be cut into the bone. A similar device can be used to pre-punch holes for the femoral component that would include two tri-flanged or quad-flanged punches for the pegs 190 and 192 combined with a flat punch for the tapered protrusions 106 of the femoral component. Punch cutting surfaces may be full depth (length) for the pegs 190 and 192 and the tapered protrusions 106 to facilitate full seating, but may be undersized with respect to a thickness to ensure a tight press fit of the implant device 100 into bone. The cutting surfaces of the device shown in FIG. 42 may additionally be angled and/or offset with respect to the opposite impaction end to allow for easier placement of the implant device 100 when the knee is approached through a limited anterior, medial, or posterior surgical approach. The impactor punch device is positioned by a trial baseplate that is precisely positioned on the cut bone surface and held in place by small pins protruding from its interior surface in contact with the cut bone and/or by pins placed through holes in the trial into the bone.

Additionally, a second impactor punch device may be used for hard bone to precisely align and "pre-cut" slots for the tapered protrusions 106 protruding from the tibial baseplate. This punch may include a full length but decreased thickness punch to ensure both full seating of the implant device 100 against the bone and tight interference fit to optimize implant initial stability and therefore allow for secondary (permanent) fixation via bone ingrowth or osseointegration. Such fin cutting structures could be sharpened, or beveled to facilitate full eating in the bone, and could be single use or multiple use. The second impactor punch device may have protrusions that fit precisely into the holes and slots previously left by the first punch above to ensure precise alignment of the smaller tapered protrusions with the peg and medial fin of the baseplate.

In further examples, a device shaped similar to the femoral component may be used, which has the same undersized full length tri-fin or quad-fin peg features designed to ensure full seating of the implant device 100 against bone with tight interference fixation. This type of device again would be positioned via corresponding peg holes on a trial component precisely affixed to the cut femoral bone via small sharp protuberances on the undersurface of the trial affixing it rigidly to the cut femoral bone, and/or pins affixing the trial to the bone. Additionally, a second punch could be available, especially for hard bone in the cut femur, to "pre-cut" the slots for the tapered protrusions protruding from the base surfaces of the femoral component, and again they would be full length but of decreased thickness to ensure both full seating of the implant device against the bone and the tight interference fit to optimize implant primary stability and secondary osseointegration. These fin cutting structures could be sharpened, or beveled to facilitate full eating in the bone, and could be single use or multiple use. The second femoral punch noted above would have protrusions that fit precisely into the two tri-flanged "holes" left by the first punch above, to ensure precise alignment of the fin structures with the pegs of the femoral component.

Following, the implant device 100 for the tibial implant is located in place, and the impactor device 204, shown in FIGS. 36-41, is used to hammer the tibial implant device into the bone. The tapered protrusions 106 create a wedge-like force upon the bony tissue, creating both positive cementless fixation and creating stimulation for bone growth to further affix the implant device 100 to the bone.

After insertion of the tibial implant device, the femoral implant device is located in place and impacted with the impactor device 204, shown in FIGS. 36-41. The impactor device 204 includes gripping fingers 206 to hold the femoral implant device, and will impart an intermittent rotation that oscillates in each direction with each hammer strike upon an impactor head of the impactor device 204. For example, as shown in FIG. 41, a zig zag channel 208 imparts a small amount of alternating twist to the impaction of the implant device 100 as the driver is struck.

Figure 43:
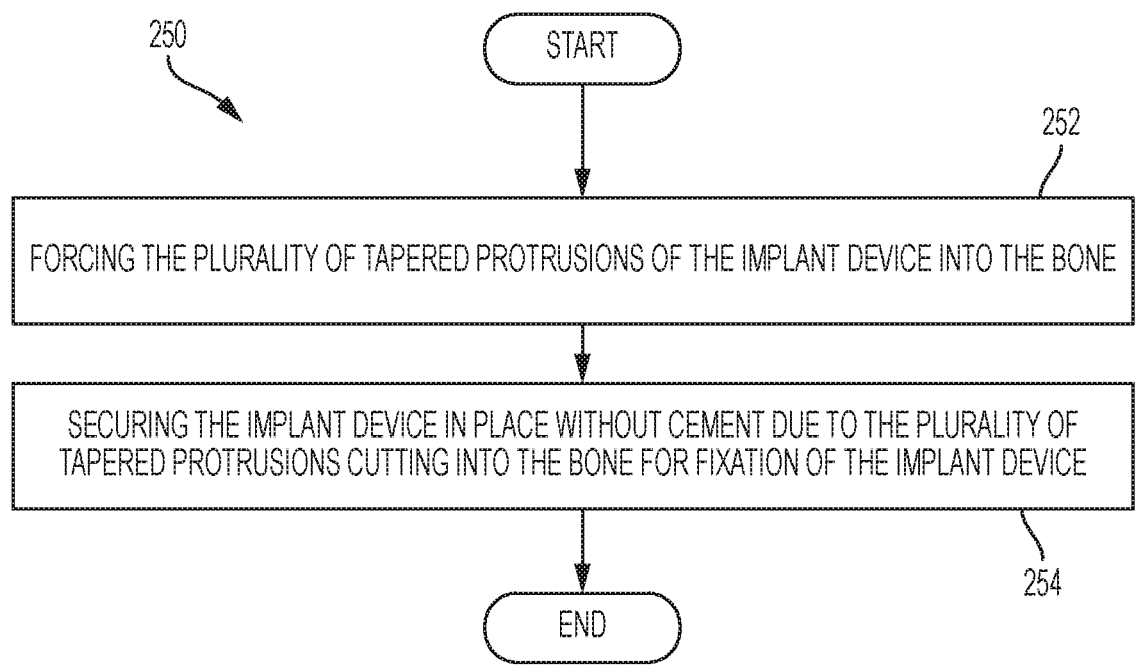
FIG. 43 shows a flowchart of an example method for inserting the implant device into bone, according to an example implementation.

FIG. 43 shows a flowchart of an example method 250 for inserting the implant device 100 into bone, according to an example implementation. Method 250 shown in FIG. 43 presents an example of a method that could be used with the implant device 100 shown in FIGS. 1-4, FIGS. 15-31, and FIGS. 33-35, and/or the impactor device 204 in FIGS. 36-41 and the impactor punch device shown in FIG. 42, for example. In some instances, components of the devices and/or apparatuses may be configured to perform the functions such that the components are actually configured and structured to enable such performance. In other examples, components of the devices and/or apparatuses may be arranged to be adapted to, capable of, or suited for performing the functions, such as when operated in a specific manner. Method 250 may include one or more operations, functions, or actions as illustrated by one or more of blocks 252-254. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 252, the method 250 includes forcing the plurality of tapered protrusions 106 of the implant device 100 into the bone. At block 254, the method 250 includes securing the implant device 100 in place without cement due to the plurality of tapered protrusions 106 cutting into the bone for fixation of the implant device 100. The implant device 100 may further include one or more pegs for seating of the implant device 100 into the bone.

Figure 44:
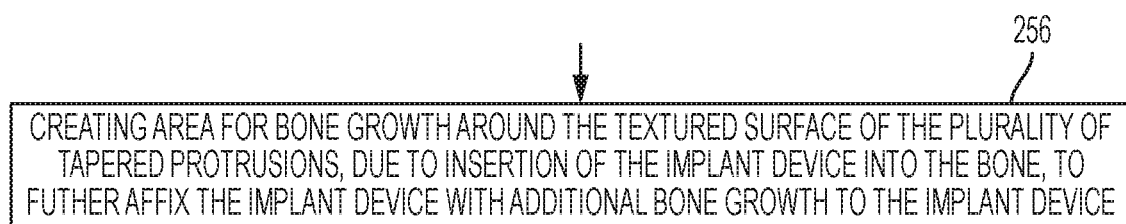
FIG. 44 shows a flowchart of an example method for use with the method shown in FIG. 43, according to an example implementation.

FIG. 44 shows a flowchart of an example method for use with the method 250, according to an example implementation. At block 256, the method 250 includes creating area for bone growth around the textured surface 108 of the plurality of tapered protrusions 106, due to insertion of the implant device 100 into the bone, to further affix the implant device 100 with additional bone growth to the implant device 100.

Example processes illustrated in the flowcharts in FIGS. 43-44 may be performed or carried out manually by a surgeon. In addition, or alternatively, example processes illustrated in the flowcharts in FIGS. 43-44 may be performed or carried out autonomously via robotic devices.

Within the examples described herein, various configurations of the implant device 100 are shown, and one configuration includes a knee implant set (e.g., the assembly shown in FIG. 32). The implant device 100 features the tapered and/or finned protrusions that cut into the bone for holding the implant device 100 in place for the near term, and encouraging bone in growth in the long term. Thus, the implant device 100 provides both rigid initial fixation (macro-fixation) and durable long-term fixation (micro-fixation). The tapered protrusions 106 can be arranged as recurring or regularly occurring structures. A shape, orientation, and rough surface of these structures increase a surface area of the implant device 100 in contact with bone, both individually and as a group, and provide for a tight interference fit of the implant device into the bone resulting in stable initial fixation, and allowing for predictable osseointegration or bone ingrowth and/or ongrowth onto a surface of the structures and the implant device 100 resulting in long-term fixation of the implant device 100 to the bone.

By the term "about", as used herein, it is meant that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide.

Different examples of the apparatus(es), device(s), and method(s) disclosed herein include a variety of components, features, and functionalities. It should be understood that the various examples of the apparatus(es), device(s), and method(s) disclosed herein may include any of the components, features, and functionalities of any of the other examples of the apparatus(es), device(s), and method(s) disclosed herein in any combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

It is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims.

What is claimed is:

1. An implant device comprising:
   a base having a surface that mates with bone; and
   a plurality of tapered protrusions positioned on the base and extending from the surface of the base that mates with bone, wherein the plurality of tapered protrusions extend in a direction perpendicular to the surface of the base and are tapered in the direction perpendicular to the surface of the base, wherein the plurality of tapered protrusions themselves have a textured or porous surface to increase area for bone growth,
   wherein the plurality of tapered protrusions are arranged on the base spaced apart by about 2 mm to about 10 mm.

2. The implant device of claim 1, wherein the textured surface includes one of a porous structure or coating, a sintered surface, a bead blasted surface, a thermal/plasma spray.

3. The implant device of claim 1, wherein the plurality of tapered protrusions have a height between about 1 mm to about 5 mm, a length between about 2 mm to about 4 cm, and a width between about 0.5 mm to about 2.5 mm.

4. The implant device of claim 1, wherein the plurality of tapered protrusions vary in height among each other.

5. The implant device of claim 1, wherein the plurality of tapered protrusions are arranged as trapezoidal blades.

6. The implant device of claim 1, wherein the plurality of tapered protrusions comprise side walls that taper inward up to about 20°.

7. The implant device of claim 1, wherein the plurality of tapered protrusions comprise:
   a bottom portion with approximately parallel side walls; and
   a top portion connected to the bottom portion, the top portion having a tapered tip.

8. The implant device of claim 7, wherein a thickness of the bottom portion is between about 0.5 mm to about 2.5 mm.

9. The implant device of claim 7, wherein the bottom portion has ends connected to the parallel side walls, and the ends slant inward toward the tapered tip.

10. The implant device of claim 7, wherein the top portion has sides and ends each slanted inward toward the tapered tip.

11. The implant device of claim 7, wherein the top portion has concave sides.

12. The implant device of claim 1, wherein the plurality of tapered protrusions have flat tips.

13. The implant device of claim 1, wherein at least some of the plurality of tapered protrusions have pointed tips.

14. The implant device of claim 1, wherein at least some of the plurality of tapered protrusions have filleted tips.

15. The implant device of claim 1, further comprising:
   a peg positioned on the base and extending from the surface of the base that mates with bone, wherein the peg is positioned between a number of the plurality of tapered protrusions.

16. The implant device of claim 15, wherein a surface of the peg is smooth and wherein a surface of the plurality of tapered protrusions includes a textured surface.

17. The implant device of claim 15, wherein a surface of the peg and a surface of the plurality of tapered protrusions includes a textured surface.

18. The implant device of claim 1, wherein the plurality of tapered protrusions vary in porosity such that a bottom portion of the plurality of tapered protrusions is more porous than a top portion of the plurality of tapered protrusions.

19. The implant device of claim 1, wherein the plurality of tapered protrusions have cutting edges that align with a direction of bone insertion.

20. The implant device of claim 1, wherein the implant device includes one of a tibia implant, a femoral implant, a unicompartmental knee replacement implant, a pelvis implant, a hip implant, a shoulder implant, an ankle implant, and a knuckle implant for a hand or foot.

21. The implant device of claim 1, wherein the base is curved and includes multiple sections on which the plurality of tapered protrusions are positioned, wherein the multiple sections are arranged such that the surface that mates with bone is a curved surface.

22. The implant device of claim 21, wherein the implant device is a femoral implant.

* * * * *